(12) United States Patent
Loterie et al.

(10) Patent No.: US 9,964,708 B2
(45) Date of Patent: May 8, 2018

(54) BENDING COMPENSATING DEVICE, SYSTEM AND METHOD FOR OPTICAL WAVEGUIDES

(71) Applicant: Ecole Polytechnique Fédérale de Lausanne (EPFL), Lausanne (CH)

(72) Inventors: Damien Loterie, Ecublens (CH); Sebastien Walpen, Lausanne (CH); Edgar Emilio Morales Delgado, Lausanne (CH); Christophe Moser, Lausanne (CH); Demetri Psaltis, Préverenges (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days. days.

(21) Appl. No.: 15/145,812

(22) Filed: May 4, 2016

(65) Prior Publication Data
US 2016/0327770 A1    Nov. 10, 2016

(30) Foreign Application Priority Data

May 6, 2015    (WO) .................. PCT/IB2015/053302

(51) Int. Cl.
| | |
|---|---|
| *G02B 23/26* | (2006.01) |
| *G02B 6/36* | (2006.01) |
| *A61B 34/00* | (2016.01) |
| *G02B 23/24* | (2006.01) |
| *G02B 6/14* | (2006.01) |

(52) U.S. Cl.
CPC .............. *G02B 6/36* (2013.01); *A61B 34/70* (2016.02); *G02B 6/14* (2013.01); *G02B 23/2476* (2013.01); *G02B 23/26* (2013.01)

(58) Field of Classification Search
None
See application file for complete search history.

(56) References Cited

U.S. PATENT DOCUMENTS

| | | | |
|---|---|---|---|
| 4,113,350 A * | 9/1978 | Haines | .................. C03C 25/106 |
| | | | 385/128 |
| 5,956,447 A | 9/1999 | Zel'dovich et al. | |
| 6,536,700 B2 * | 3/2003 | Watson | .................. B65H 55/04 |
| | | | 226/44 |

(Continued)

FOREIGN PATENT DOCUMENTS

JP    2009101076 A *    5/2009    ......... A61B 1/00039

OTHER PUBLICATIONS

Anderson, D. Z., M. A. Bolshtyansky, and B. Ya Zel'dovich. "Stabilization of the speckle pattern of a multimode fiber undergoing bending." Optics letters 21.11 (1996): 785-787.

(Continued)

*Primary Examiner* — Michelle R Connelly
(74) *Attorney, Agent, or Firm* — Andre Roland S.A.; Nikolaus P. Schibli (57) ABSTRACT

A bending compensation device for a waveguide, including a direction changing device configured to maintain a constant bending angle to the waveguide, a distal end of the waveguide having a first orientation, and the proximal end of the waveguide having a second orientation, and a motion device connected to the direction changing device, the motion device configured to move the direction changing device upon a movement of the waveguide.

12 Claims, 8 Drawing Sheets

(56) References Cited

U.S. PATENT DOCUMENTS

2006/0109519 A1* 5/2006 Beselt ............... G01N 21/3554
358/442

OTHER PUBLICATIONS

Caravaca-Aguirre, Antonio M., et al. "Real-time resilient focusing through a bending multimode fiber." Optics express 21.10 (2013): 12881-12887.
Choi, Youngwoon, et al. "Scanner-free and wide-field endoscopic imaging by using a single multimode optical fiber." Physical review letters 109.20 (2012): 203901.
• ižmár, Tomáš, and Kishan Dholakia. "Exploiting multimode waveguides for pure fibre-based imaging." Nature communications 3 (2012): 1027.
Farahi, Salma, et al. "Dynamic bending compensation while focusing through a multimode fiber." Optics express 21.19 (2013): 22504-22514.
Papadopoulos, Ioannis N., et al. "High-resolution, lensless endoscope based on digital scanning through a multimode optical fiber." Biomedical optics express 4.2 (2013): 260-270.

* cited by examiner

BENDING COMPENSATING DEVICE, SYSTEM AND METHOD FOR OPTICAL WAVEGUIDES

CROSS-REFERENCE TO RELATED APPLICATIONS

The present Application claims foreign priority to the International patent application with the serial number PCT/IB2015/053302 filed on May 6, 2015, the entire contents of which is herewith incorporated by reference.

FIELD OF THE INVENTION

The present invention relates to a device and a system for preserving transmission characteristics of optical fibers, waveguides, multimode waveguides such as optical waveguides or waveguide bundles, endoscopic devices, when the same are subject to mechanical motion, and related to a method of preserving transmission characteristics.

BACKGROUND

Optical waveguides had a profound impact on modern telecommunications, but are increasingly being used for other applications as well. For example, fiber-based endoscopy systems are used in medicine to view remote locations within the body. Advantages of optical fibers are that they can guide light over significant distances with low loss, they are flexible, they are very thin, they have a low cost, and they are made of inert, non-toxic materials.

Optical waveguides can be classified according to the transverse modes of propagation they support. A mode can be seen as a spatial configuration of light that is allowed to propagate within the waveguide. Single-mode waveguides have only one mode, meaning that light can only be guided through the waveguide with one predefined spatial distribution. In single-mode waveguides, information can only be transmitted modulating the light signal in time, and it is not possible to directly transmit spatial information such as images, because the spatial shape of light is fixed.

Multimode waveguides on the other hand support multiple transverse modes, meaning that the light can be guided with a variety of spatial configurations. Each mode has different propagation characteristics within the waveguide, because of modal dispersion and modal mixing. As a consequence, the spatial configuration of the light at the input of the waveguide is not maintained until the output. However, if the propagation characteristics of each mode within the waveguide are known by either measurement or calculation, it is possible to transmit spatial information such as images.

One problem in multimode waveguide imaging systems is caused when the waveguide is subject to bending. As a consequence, the propagation characteristics of the multiple modes change relatively to each other depending on the geometrical configuration of the waveguide. While the characteristics can be calculated or measured in advance for one particular bending state of the waveguide, the same data is not valid for other bending states. This limits the flexibility of multimode waveguides as imaging devices, e.g. in the context of endoscopy.

U.S. Pat. No. 5,956,447 proposes to divide the waveguide in two parts, a pre-bent auxiliary part, and a work part. The work part can be used for flexible imaging. Bends incurred in the work part of the waveguide can be compensated by loosening the pre-bending of the auxiliary part. However, in practice, it can be difficult to precisely compensate bending in a freely moving waveguide. The required compensations must be found by trial and error, and a very involved mechanical system would be needed to compensate all the integrals of curvature completely.

Accordingly, in light of the above discussed deficiencies of the background art, there is a strong need to provide for systems, devices and methods to improve existing solutions to compensate for bending that is applied to a waveguide.

SUMMARY

According to one aspect of the present invention, a bending compensation device for a waveguide is provided. Preferably, the device includes a direction changing device configured to maintain a constant bending angle to the waveguide, a distal end of the waveguide having a first orientation, and the proximal end of the waveguide having a second orientation, and a motion device connected to the direction changing device, the motion device configured to move the direction changing device upon a movement of the waveguide.

According to another aspect of the present invention, a device is provided that preferably constrains the waveguide in such a way that it is always subjected to the same bending, while permitting movement in the tip of the waveguide. The movement of the tip is obtained by varying the position of the bends along the length of the waveguide. Because the bends are fixed, but are only moved along the waveguide, all the bending integrals along the waveguide remain constant. Therefore, the relative propagation characteristics of the modes do not change. When used for endoscopic imaging, it is possible to image continuously through the multimode waveguide without recalibration.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

Figure 1:
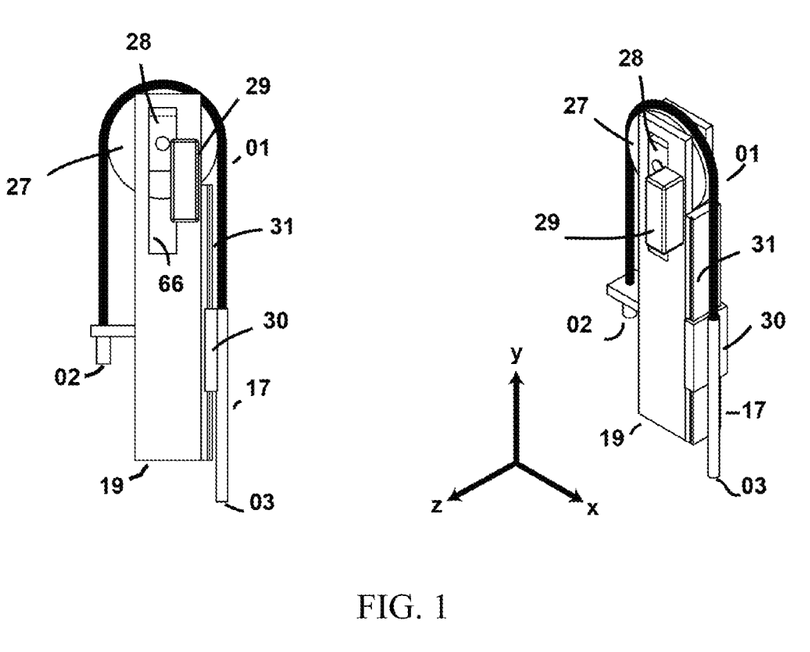
FIG. 1 depicts a schematic perspective representation of exemplary embodiment of the device according to one aspect of the present invention, showing an optical waveguide 01 whose proximal tip 02 can be fixed, while distal tip 03 of waveguide 01 can move along the Y-axis direction and the sum of the curvature of the waveguide 01 remains identical.

In a first preferred embodiment the apparatus comprises an optical waveguide 01 held by a single pulley 27 as shown in the schematic perspective view of FIG. 1. Proximal end or tip 02 can be fixed, for example, to a wavefront shaping setup (not shown). The distal tip 03 of the waveguide is fixed to a rigid hollow needle like structure 17. The needle like structure 17 forms a tube or sheath around fiber 01 at the distal end or top 03. Fiber 01 is held by a pulley 27 which is carried by a carriage 28 that can slide in the aperture 66, pulley 27 defining a bending radius of waveguide 01 that corresponds to a radius of pulley 27. Pulley 27 can rotate freely around its rotational axis. The linear movement of the distal tip 03 of the fiber can be followed by displacement of carriage 28 by motor or linear actuator 29. Needle 17 can be attached to carriage 30 which is capable of sliding in a linear movement along rail 31 so that distal tip 03 of waveguide 01 moves in Y-axis direction. With this arrangement, distal tip 03 can move while the bending radius or the sum of the curvature of the waveguide 01 remains identical. For references purposes, within the figures, an X-Y-Z reference coordinate system is shown. Because the waveguide bending is the same and preserved throughout the movement of waveguide 01 along the Y axis, the light transmitted from proximal end 02 to distal end 03 of the waveguide 01 or vice versa is not altered by the displacement along the Y direction of the distal end 03 of the waveguide 01.

With the device or system explained above, it is possible to compensate the bending of an optical waveguide 01 as the waveguide 01 is moved, in such a way that the propagation characteristics of light transmitted through the waveguide 01 remain constant as the waveguide 01 is moved. For this purpose, a pulley 27 is configured to move relative to the movement of waveguide 01, for example by a passive mechanical system or an active one that measures the movement of waveguide, and actively moves pulley 27 with motors. When an optical waveguide 01 is subjected to bending, phase delays are introduced to the propagating field, leading to a bending dependence of the intensity of the field delivered to the other end of the waveguide 01. As explained above, with the features of the embodiments of the present invention, it is possible to remove such propagation dependence on waveguide bending by using a device or system that preserves a constant bending along the waveguide as the waveguide 01 is moved.

The device or system shown in FIG. 1 is shown as an exemplary embodiment, and it is understood that one of ordinary skill in the art will be able to design alternative arrangements of the bending compensation mechanism such as different orientations, difference position of pulleys, different sizes of pulleys, or combination of at least one pulley and a rigid jacket, such as, but not limited to, a needle, or several rigid jackets, without departing from the scope specified in the claims of the present invention. For example, it is possible that the device of FIG. 1 be used for, but not limited to, a step-index fiber, a graded index fiber, a double-clad fiber, a large mode area fiber, a fiber bundle, a no-core fiber, a rod, and a single mode fiber.

Theoretical analyses indicate that the relative propagation characteristics of modes are determined by integrals of the radius of curvature along the waveguide. These integrals can be expressed by the following mathematical equation:

$$\int_0^L \frac{1}{R^n(l)} dl$$

In this equation, L is the length of the waveguide segment under consideration, R(l) is the local radius of curvature of the waveguide at a position l along the waveguide, and n is an even number. Herein, the set of these integrals are referred to as "bending". A waveguide is considered to have the same bending as long as the values of these integrals do not change. With the features of the embodiments of the present invention, it is possible to constrain the optical waveguide 01 in a bending-compensating structure, while all bending radii are predefined and fixed, regardless of the exterior translations and angular orientations that are applied to the waveguide. The device maintains the curvature integrals constant while allowing free movement of end of the waveguide.

Figure 2:
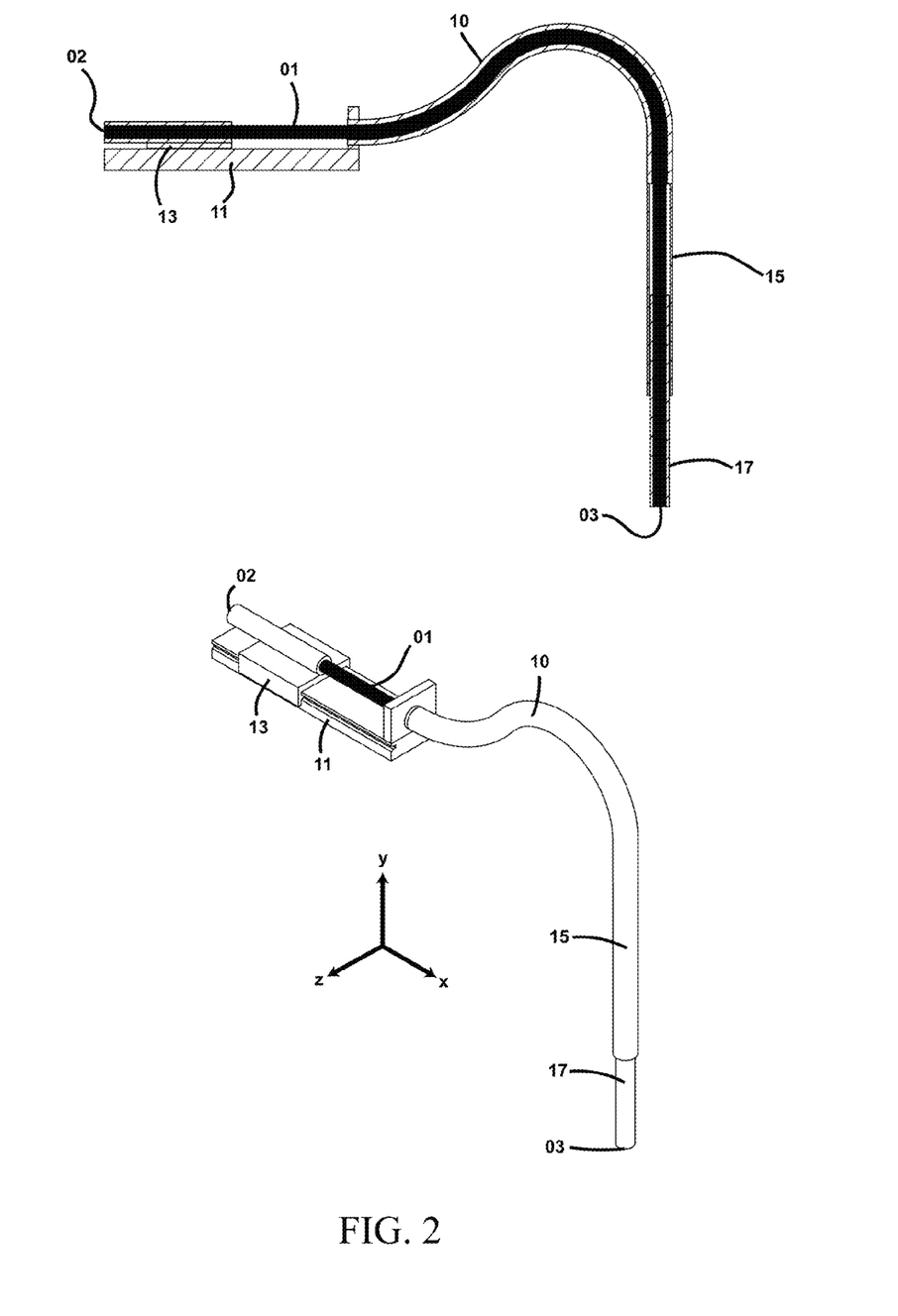
FIG. 2 depicts a schematic perspective representation of an exemplary embodiment according to another aspect of the present invention, showing a translation movement with a rigid jacket, where proximal tip 02 is fixed, and rigid guide 10 moves along a direction of the X-axis. Distal tip 03 of waveguide 01 moves in X-axis and Y-axis direction, while the bending radius of the waveguide 01 remains identical due to rigid guide 10.

Next, FIG. 2 shows a schematic perspective view of another embodiment of the present invention, in which a device is shown that includes an optical waveguide 01 that can slide freely within a rigid jacket, guide, or sheath 10. Proximal end 02 of waveguide 01 can be fixed, for example, to a wavefront shaping setup (not shown). Carriage 13 of a translation guide 11 allows to slide optical waveguide 01 inside the jacket 10. This causes a translation of the distal end 03. Distal end 03 of waveguide 01 is fixed rigidly in a rigid needle-like hollow structure 17, that slides freely within longitudinal portion 15 of rigid jacket 10. In this embodiment, a linear motion of distal end 03 of waveguide 01 can be obtained by a corresponding linear motion of proximal end 02, without changing any bending during this motion. The initial bending state of jacket 10 can be chosen freely depending on the desired direction of the motion.

Figure 3:
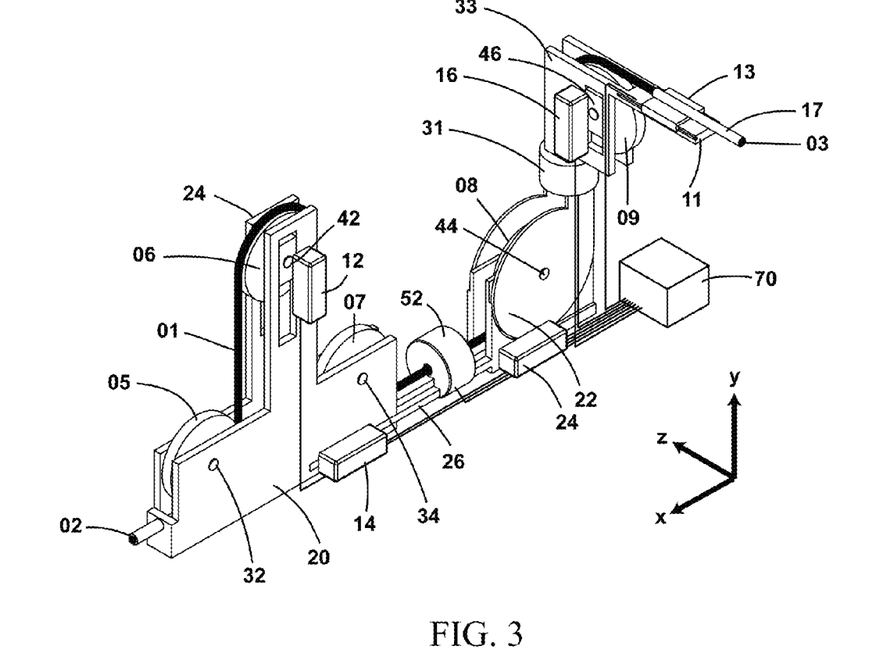
FIG. 3 depicts a schematic perspective view of a system according to an aspect of the present invention, the system configured to provide a constant bending radius to all the portions of the waveguide, with a first, constant orientation direction of proximal tip 02, and a variable orientation direction of distal tip 03, distal tip 03 moveable in any direction in the three-dimensional space.

Moreover, FIG. 3 shows an another embodiment of the present invention, with a device or system including an optical waveguide 01 held by a set of five (5) pulleys 05, 06, 07, 08, 09. Proximal end 02 of waveguide 01 can be fixed, for example, to a wavefront shaping setup (not show), and therefore has a fixed orientation. All pulleys 05, 06, 07, 08, 09 are freely rotatable around a corresponding rotatable axis, with axes 32, 34 for pulleys 05, 07, respectively, having a fixed position with respect to each other, while axes 42, 44, and 46, for pulleys 06, 08, and 09, respectively can move linearly with corresponding linear motors or actuators 12, 14, 16. The fixed axes 32, 34, and linearly movable axes 42, 44, 46 of pulleys 05, 06, 07, 08, 09 are mounted to a frame 20, frame 20 including a translatable bottom arm 26, a fixed Y-arm 24, and a tiltable and rotatable arm 22. Fixed axes 32, 34 are rotatably attached to the frame 20 at fixed positions of rotational axes 32, 34. Y-arm 24 includes a linear motor device 12 that can linearly move axis 42 along the Y-axis, Y-arm 24 being fixed, or integrally formed with frame 20, and linear movable axis 42 of pulley 06 is attached to the base of linear motor device 12 so that linear movable axis 42 can be displaced along the Y-axis.

Moreover, a linear motor device 14 is arranged on bottom arm 26 of frame 20 such that bottom arm 26 can be moved along the X-axis relative to frame 20. Linear movable axis 44 of pulley 08 is attached to the base of linear motor device 14, so that axis 44 can be moved linearly along the X-axis. Rotatable and tiltable arm 22 is movably attached to bottom arm 26, such that three different movements can be performed. First, arm 22 is attached to linear motor device 14 such that it can be moved back and forth along the X-axis at a position that corresponds to a position of the linear movable axis 44 and the position of pulley 08. Second, independent of the first movement, arm 22 can turn or rotate back and forth perpendicularly to the X-axis, by a rotation device 52 that is arranged between the rotatable and tiltable arm 22 and the base of the linear motor device 14. The axis of rotation of rotatable and tiltable arm 22 is defined by rotation device 52, and corresponds to an axis formed by a longitudinal extension of waveguide 01 in a section between pulley 07 and pulley 08. Third, independent to the first and the second movement, rotatable and tiltable arm 22 can tilt or turn around a rotatable axis 44 around the X-axis by a rotation device 24.

Both pulley 08 and pulley 09 are moved with a change in position of rotatable and tiltable arm 22. This requires that linear motor device 16 is attached and can tilt or rotate with rotatable and tiltable arm 22. Rotation device 24 is attached to rotation device 52 and can be moved, together with rotatable and tiltable arm 22 linearly along the X-axis with linear motor device 14. Also, a rotatable arm 33 is attached to rotatable and tiltable arm 22 via a rotation device 31. This device allows for a third rotation along the axis formed by a longitudinal extension of waveguide 01 in a section between pulley 08 and 09. Rotation devices 22, 24, 31, 52, can be made of a rotative stepper or servo motor, and linear motor devices 12, 14, 16 can be made by linear actuators or linear servos. In a variant, the turning motion of rotation devices 22, 24, 32, 52 and linear motion of linear motor devices 14, 16 can done by a multiaxial robot.

A linear motor device 16 is arranged with rotatable arm 33, and allows to move a base and the linear movable axis 46 of pulley 09 along an axis that is defined by a longitudinal extension of rotatable and tiltable arm 33. With linear motor device 16 that can linearly displace pulley 09 along rotatable and tiltable arm 33 relative to platform 22, rotation device 24 that allows to tilt, turn or rotate rotatable and tiltable arm 22 around rotatable axis 44, rotative device 52 that allows to turn or rotate rotatable and tiltable arm 22 around its own axis of longitudinal extension, and linear motor device 14 that allows to linearly move rotatable and tiltable arm 22 along the X-axis, pulley 09 has the largest degree freedom for positioning, and can be subjected to a wide range of angular and spatial positions. Distal tip 03 of waveguide 01 is fixed in a rigid needle-like structure 17 on a carriage 13 that can be moved linearly along a rail 11 for example by a motor. With these movement stages, the distal tip 03 of waveguide 01 has full translational and rotational freedom while the waveguide 01 can be maintained in a constant bending state.

A control device 70 can be arranged that controls all positions of linear motor devices 12, 14, and 16, and rotation devices 22, 24, 31, 52 and also possibly receives a measurement signal from sensors. For example, two linear photo arrays and two linear laser projectors can be used along two different axes Y and X, respectively, to detect a position of distal end 03 of waveguide 01, and this measurement signal can be provided to control device 70. Control device 70 is equipped with a processor that allows to perform fast closed loop control with a high sampling rate, so that a position of distal end 03 of waveguide 01 can be followed with the system, to maintain a constant bending radius that is defined by a radius of pulleys 05, 06, 07, 08, 09.

Figure 4:
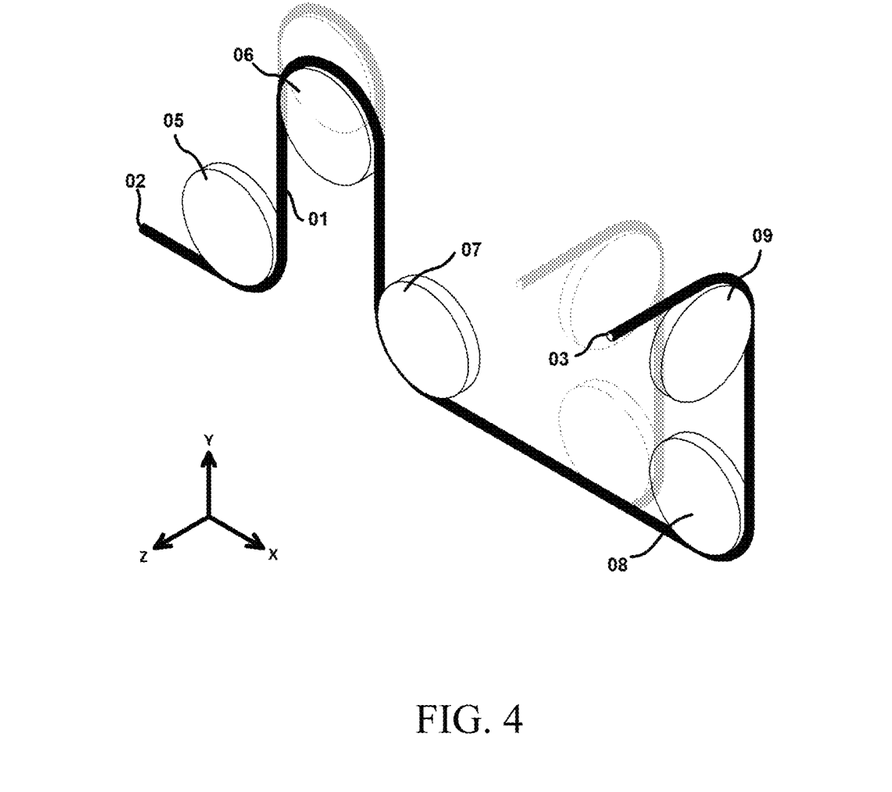
FIG. 4 depicts a schematic perspective view of the system of FIG. 3 without the actuators, performing X-axis translation according to still another aspect of the present invention, where proximal tip 02 is fixed, pulleys 05 and 07 are fixed, and pulleys 08 and 09 move along the X-axis. Pulley 06 moves up and down along the Y-axis to compensate for the Z position of waveguide 01. Distal tip 03 of the waveguide 01 moves along the X-axis. The bending radius of waveguide 01 remains identical.
Figure 5:
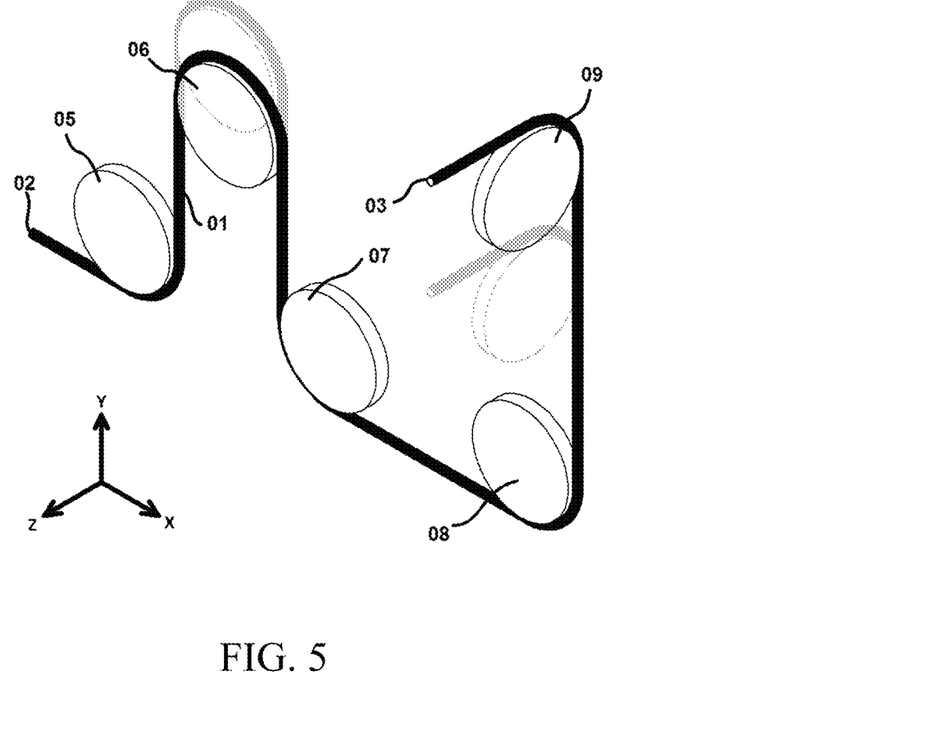
FIG. 5 depicts a schematic perspective view of the system of FIG. 3 without the actuators, performing Y-axis translation according to yet another aspect of the present invention, where proximal tip 02 is fixed, pulleys 05, 07 and 08 are fixed, and pulley 09 moves along the Y-axis. Pulley 06 moves up and down along the Y-axis to compensate for the Z position of waveguide 01. Distal tip 03 of waveguide 01 moves along the Y-axis. The bending radius of the waveguide 01 remains identical.
Figure 6:
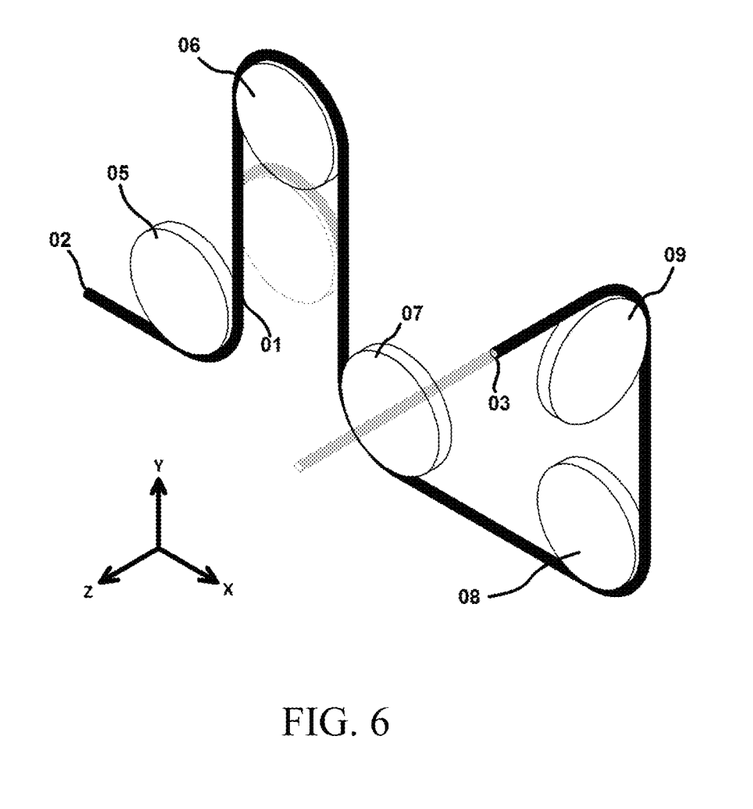
FIG. 6 depicts a schematic perspective view of the system of FIG. 3 without the actuators, performing Z-axis translation according to still another aspect of the present invention, where proximal tip 02 is fixed, pulleys 05, 07, 08 and 09 are fixed, and pulley 06 moves up and down along the Y-axis. Distal tip 03 of waveguide 01 moves along the Z-axis. The bending radius of waveguide 01 remains identical.
Figure 7:
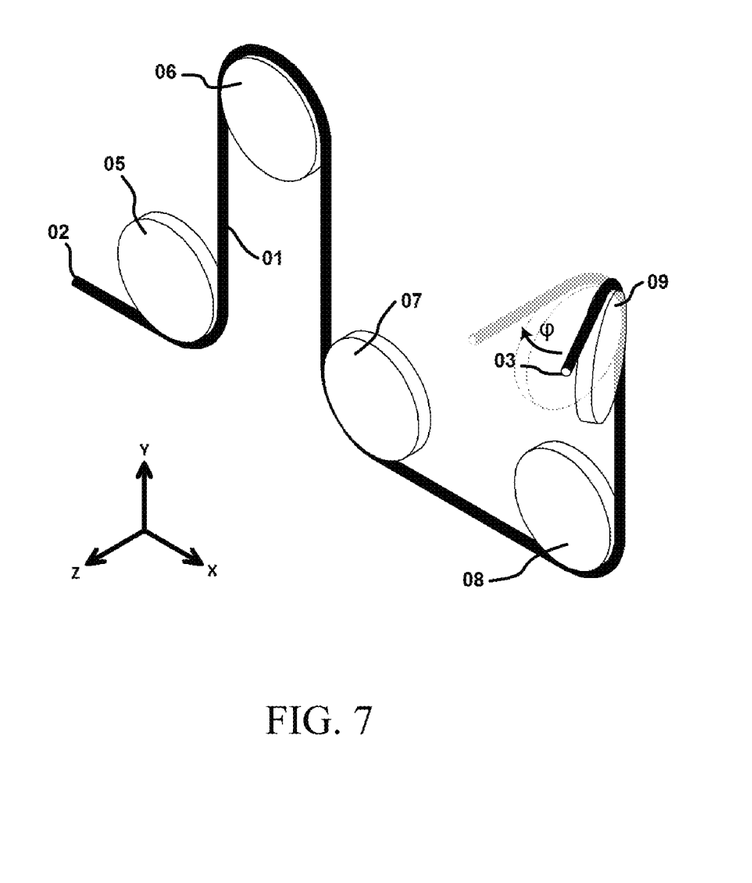
FIG. 7 depicts a schematic perspective view of the system of FIG. 3 without the actuators, performing φ rotation according to still another aspect of the present invention, where proximal tip 02 is fixed, pulleys 05, 06, 07 and 08 are fixed, and pulley 09 rotates in the φ direction. Distal tip 03 of waveguide 01 rotates in the φ direction. The bending radius of waveguide 01 remains identical.
Figure 8:
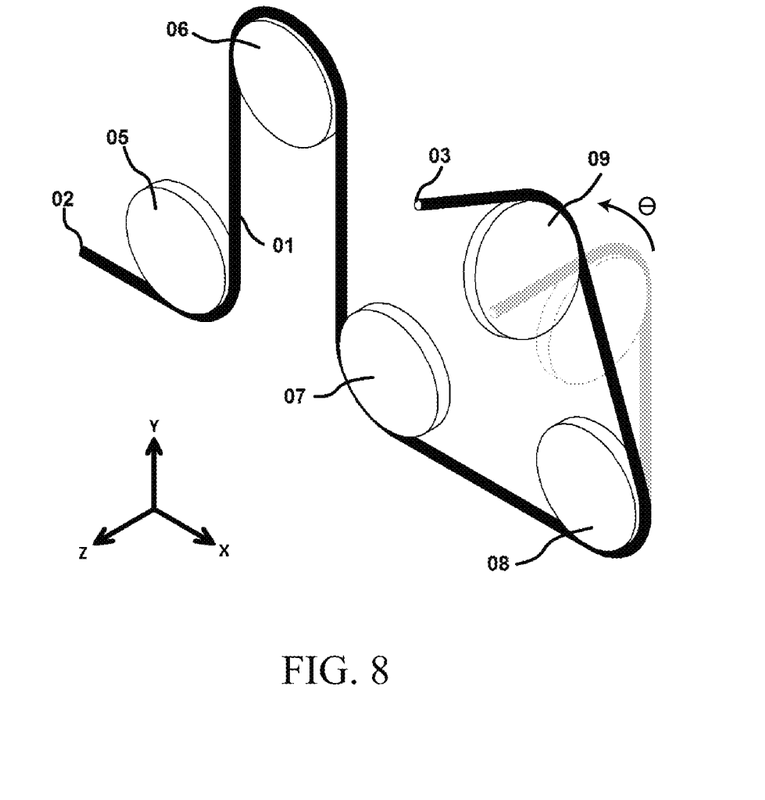
FIG. 8 depicts a schematic perspective view of the system of FIG. 3 without the actuators, performing Θ rotation according to another aspect of the present invention, where proximal tip 02 is fixed, pulleys 05, 06, 07 and 08 are fixed, and pulley 09 rotates in the Θ direction. Distal tip 03 of waveguide 01 rotates in the Θ direction. The bending radius of waveguide 01 remains identical.

With this system shown in FIG. 3, the following five (5) movements of distal end 03 of waveguide 01 can be accomplished the following way. First, as shown in FIG. 4, a movement of distal end 03 of waveguide 01 in the X direction is accomplished by movement of pulley 06 in the Y direction and a movement of pulleys 08 and 09 in the X direction. With this relative movement of pulleys 06, 08, and 09, which results in a shortening of a portion of the waveguide that is located between pulleys 07 and 08, and lengthening two portions that are located between pulley 05 and pulley 06, and between pulley 07 and pulley 06, no bending radius of waveguide 01 is changed, despite distal end 03 of waveguide 01 moving in a negative X-direction. Without the proposed device, a bending radius of the waveguide, arranged in a plane formed by the X and Z axes, would change. Second, as shown in FIG. 5, a movement of distal end 03 of waveguide 01 in the Y direction is accomplished by movement of pulley 06 in the Y direction and movement of pulley 9 in the y direction. Third, as shown in FIG. 6, a movement of distal end 03 of waveguide 01 in the Z direction is accomplished by movement of pulley 06 in the y direction and movement of the distal end 03 in Z direction. This allows to apply a force in the Z-direction to distal end 03 that leads to a movement of the waveguide in the Z-direction, and the device shown can compensate for the application of that force and movement without that additional mechanical tensile stress is applied to waveguide, and without that the geometry of distal end 03 and proximal end 02 are modified. Fourth, as shown in FIG. 7, rotation of distal end 03 of waveguide 01 in φ direction is accomplished by rotation of pulley 09 in the φ direction. Angular orientation of distal end 03 thereby changes with respect to angular orientation of proximal end 02, however, no bending radii are changed. Without the device as shown, a bending radius of the waveguide would be changed, as the angular orientation would lead to a different bending radius between proximal end 02 and distal end 03. Fifth, as shown in FIG. 8, movement of distal end 03 of the waveguide 01 in the Θ direction is accomplished by rotation of pulley 09 in the Θ direction.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A bending compensation device for a waveguide that is used for imaging, the waveguide having a fixed proximal end and a distal end that can move relative to the fixed proximal end, comprising:
   an attachment device for fixedly attaching the proximal end of the waveguide, the distal end of the waveguide configured to move at least one of a position and orientation during imaging;
   a direction changing device configured to maintain a constant bending angle to the waveguide; and
   a motion device including a linear motor and rotation device that are operatively connected to the direction changing device, the motion device configured to move at least one of a position and an axis of orientation of the direction changing device upon a movement of the distal end of the waveguide.

2. The bending compensation device according to claim 1, wherein the direction changing device includes a pulley.

3. The bending compensation device according to claim 1, wherein the direction changing device includes at least five pulleys, two of the five pulleys having a fixed position to each other, three of the five pulleys having variable positions with respect to the two fixed pulleys.

4. The bending compensation device according to claim 1, wherein the linear motor of the motion device is configured to move the direction changing device along a linear axis.

5. The bending compensation device according to claim 1, wherein the waveguide includes at least one of selected from the group: a step-index fiber, a graded index fiber, a double-clad fiber, a large mode area fiber, a fiber bundle, a no-core fiber, a rod, and a single mode fiber.

6. The bending compensation device according to claim 1, wherein the direction changing device includes a sheath that slidably supports the waveguide.

7. The bending compensation device according to claim 1, wherein the proximal end of the waveguide is fixedly attached relative to a frame that holds the direction changing device.

8. The bending compensation device according to claim 1, wherein the proximal tip of the waveguide is fixed to wavefront shaping setup.

9. The bending compensation device according to claim 1, wherein the proximal tip of the waveguide is fixed relative to a frame to prevent any movement of the proximal tip relative to frame.

10. The bending compensation device according to claim 1, wherein rotation device includes at least one of a stepper motor, a servo motor and a multi-axial robot.

11. A bending compensation device for a waveguide used for imaging having a proximal end and a distal end, the distal end of the waveguide configured to move at least one of a position and an orientation relative to the proximal end, the device comprising:
    an attachment device for fixedly attaching the proximal end of the waveguide;
    a direction changing device configured to maintain a constant bending angle to the waveguide; and
    a motion device connected to the direction changing device, the motion device configured to move the direction changing device upon a movement of the distal end of the waveguide,
    wherein the direction changing device includes at least five pulleys, two of the five pulleys having a fixed position to each other, three of the five pulleys having variable positions with respect to the two fixed pulleys.

12. A bending compensation device for a waveguide used for imaging having a proximal end and a distal end, the distal end of the waveguide configured to move at least one of a position and an orientation relative to the proximal end, the device comprising:
    an attachment device for fixedly attaching the proximal end of the waveguide;
    a direction changing device configured to maintain a constant bending angle to the waveguide; and
    a motion device connected to the direction changing device, the motion device configured to move the direction changing device upon a movement of the distal end of the waveguide,
    wherein the direction changing device includes a sheath that slidably supports the waveguide.

* * * * *